(12) United States Patent
Molino et al.

(10) Patent No.: US 6,764,521 B2
(45) Date of Patent: Jul. 20, 2004

(54) MULTI-AXIAL ANKLE JOINT

(76) Inventors: Joseph L. Molino, 2 Aura Dr., Valley Cottage, NY (US) 10989; Michael Rebarber, 28 Buckingham Pl., Glen Rock, NJ (US) 07452

( * ) Notice: Subject to any disclaimer, the term of this patent is extended or adjusted under 35 U.S.C. 154(b) by 172 days.

(21) Appl. No.: 09/938,427

(22) Filed: Aug. 24, 2001

(65) Prior Publication Data

US 2003/0040810 A1 Feb. 27, 2003

(51) Int. Cl.[7] ............................ A61F 2/66; A61F 2/64
(52) U.S. Cl. ..................... 623/52; 623/49; 623/47
(58) Field of Search .............................. 623/48, 47, 49, 623/52, 53, 55

(56) References Cited

U.S. PATENT DOCUMENTS

| | | | |
|---|---|---|---|
| 2,208,275 A | | 7/1940 | McCann |
| 2,692,990 A | * | 11/1954 | Schaefer ..................... 623/49 |
| 3,779,654 A | | 12/1973 | Horne |
| 3,871,032 A | | 3/1975 | Karas |
| 4,446,580 A | | 5/1984 | Furuya et al. |
| 4,461,045 A | * | 7/1984 | Shorter et al. ................ 623/40 |
| 5,030,239 A | | 7/1991 | Copes |
| 5,181,931 A | | 1/1993 | van de Veen |
| 5,443,527 A | | 8/1995 | Wilson |
| 5,571,210 A | | 11/1996 | Lindh |
| 5,571,212 A | | 11/1996 | Cornelius |
| 5,695,526 A | * | 12/1997 | Wilson ........................ 623/49 |
| 5,728,175 A | * | 3/1998 | Rincoe ........................ 623/49 |
| 5,800,566 A | | 9/1998 | Gramnas |
| 5,800,567 A | | 9/1998 | Cooper et al. |
| 6,077,301 A | | 6/2000 | Pusch |
| 6,080,197 A | * | 6/2000 | Chen ........................... 623/27 |
| 6,129,766 A | * | 10/2000 | Johnson et al. ............... 623/49 |
| 6,187,052 B1 | | 2/2001 | Molino et al. |
| 6,436,149 B1 | * | 8/2002 | Rincoe ........................ 623/47 |

FOREIGN PATENT DOCUMENTS

FR    2 653 327    4/1991

* cited by examiner

Primary Examiner—Alvin Stewart
(74) Attorney, Agent, or Firm—Lawrence G. Fridman

(57) ABSTRACT

A prosthetic ankle joint consists of a base which includes an upper base portion and a lower base portion. The lower base portion is formed with a substantially hollow receiving cavity extending inwardly from an end thereof remote from the upper base portion. A base member is movably positioned within the receiving cavity and is connected to a prosthetic foot. The base member is movable in side-to-side direction independently of the base, so as to enable the prosthetic foot to closely follow a walking surface. The motion of the base member is controlled by resilient biasing members positioned between the inner cavity and the base member.

20 Claims, 7 Drawing Sheets

MULTI-AXIAL ANKLE JOINT

FIELD OF THE INVENTION

This invention relates in general to prosthetic devices, and more particularly to articulated prosthetic ankle joints.

BACKGROUND OF THE INVENTION

Each foot and ankle during walking travel through stance and swing phases of a gate cycle. In the stance phase, the foot is in contact with the ground and the weight of a person is supported on the foot. In the swing phase, the foot is off the ground as the entire leg and foot move from a posterior position to an anterior position with respect to a center of gravity of the person. The stance phase begins just after completion of the swing phase and commences with a heel strike wherein the foot is lowered to the ground as the body moves forward from a position posterior to the person's center of gravity. Immediately after heel strike, the foot moves from a dorsiflexed position, wherein the toes of the foot are pointed upwards, to a plantarflexed position wherein the bottom of the foot or shoe is flat on the walking surface, which provides greater stability as the entire weight of the person is shifted over the foot in contact with the ground. The swing phase commences just after heel strike of the other foot. During the swing phase, the foot is again in the dorsiflexed position as the foot leaves the walking surface and the foot and leg swing forward in preparation for the stance phase. Dorsiflexion is essential for normal human locomotion, since the toes must be dorsiflexed in order to clear the floor. If the foot were not dorsiflexed during the swing phase, it would most likely catch on the walking surface and cause the person to stumble and fall, leading to potentially serious injury.

For the purposes of this disclosure, the term medial refers to the person's center of gravity, whereas the medial movement is the sidewise, inward movement toward the center of gravity. The term lateral motion is defined herein as the sidewise outward movement from the center of gravity. In the neutral or medial position the interior and exterior parts of the foot are positioned substantially horizontally. Two inclined positions of the human foot in both directions from the vertical are defined herein as inversion and eversion. The inversion or inverted position occurs when an exterior part of the foot is sloped downwardly, while an interior part of the foot is directed upwardly. In the opposite respect, the eversion or inverted position of the foot occurs when the exterior part of the foot is directed upwardly and the interior part of the foot slopes downwardly. The inclination of the human foot in the inverted and everted positions ranges between 0° and 15° to the horizontal plane.

There are currently available prosthetic ankle joints which are designed to assist a user during walking or travel through stance and swing phases of a gait cycle. An example of such modern prosthetic ankle joint is provided by U.S. Pat. No. 6,187,052 which is incorporated by reference by the present application. However, the movements of the human foot are so complex, so that even this sophisticated prosthetic device does not imitate some important aspects of the human ankle movement during walking. In this respect, the available prior art prosthetic ankle joints are not fully capable of movement from side to side, so as to encompass the required range of movements of the human ankle in the above-discussed inversion and eversion positions accompanied by the controlled return thereof to the medial or neutral position. Therefore, the known prior art prosthetic devices cannot efficiently accommodate a combination of slopes in sideward fashion that act upon the bottom of the foot during travel by an amputee.

Thus, it has been long felt and unsolved need for a prosthetic ankle unit which is capable of imitating important aspects of the human ankle movements during walking including inclined positions such as the inversion and eversion movements, so as to enable the prosthetic foot to accommodate slopes and other types of uneven terrain. In the present invention this is accomplished by positioning of a base member between resilient biasing members, so as to provide a multi-axial, self-centered prosthetic ankle joint, which, after achieving such inclined positions, tends to return the base member and the prosthetic foot connected thereto to the medial or neutral state.

SUMMARY OF THE INVENTION

One aspect of the invention provides a prosthetic ankle joint for connection between a pylon and a prosthetic foot. The prosthetic ankle joint includes a base member which consists of an upper base portion and a lower base portion. The lower base portion is formed with a substantially hollow receiving inner cavity extending inwardly from an end thereof remote from the upper base portion. The base member is movably positioned within the receiving inner cavity and is connected to a prosthetic foot. The base member is movable in the side-to-side direction relative to the base, so as to enable the prosthetic foot to closely follow a walking surface.

As to another aspect of the invention, the base member has an inverse T-shaped configuration and is arcuately movable within the receiving inner cavity. The base member comprises of an upright portion which extends outwardly from a lower portion in such a manner that first and second lower engaging portions are formed on either side of the upright portion. The first upper engaging portion and the first lower engaging portion define a first engaging zone and the second upper engaging portion and the second lower engaging portion define a second engaging zone.

As to a further aspect of the invention, a pair of resilient biasing members are freely positioned within the inner cavity, so as to face the respective first and second engaging zones of the base member. The first upper engaging portion is preferably substantially normal to the first lower engaging portion and the second upper engaging portion is preferably substantially normal to the second lower engaging portion.

Still another aspect of the invention provides the prosthetic ankle joint wherein coaxial apertures are formed within the anterior and posterior walls of the lower base portion. The upright portion of the base member contains an opening passing therethrough. The base member is movably supported within the lower base portion by a shaft passing through the aperture in the anterior and posterior walls and the opening in the upright portion.

A Still further aspect of the invention provides the prosthetic ankle joint, wherein an enclosed area is defined within the inner receiving cavity in one direction by the pair of biasing members facing the engaging zones; and in the other direction the enclosed area is defined by the inner surface of the anterior and posterior walls positioned in the vicinity of substantially flat anterior and posterior surfaces of the base member. During the arcuate motion of the base member a distance between the respective engaging zone of the base member and the inner cavity is decreased causing deformation of the respective biasing member interposed therebetween. The deformed biasing member forces the base member to return to a neutral position in which a vertical axis of the base member substantially coincides with the vertical axis of the base.

As to a still further aspect of the invention, a prosthetic ankle joint is provided which includes a base consisting of an upper base portion and a lower base portion. The lower base portion is formed with a substantially hollow receiving inner cavity extending inwardly from an end thereof remote from the upper base portion. A base member is movably positioned within the receiving cavity and is connected to a prosthetic foot. The base member has an inverse T-shaped configuration and comprises an upright portion which extends outwardly from the lower portion in such a manner that first and second engaging zones are formed on either side of the base member. A pair of resilient biasing members is provided within the receiving inner cavity, so as to face the respective first and second engaging zones and is adapted to limit and control the arcuate motion of the base member.

BRIEF DESCRIPTION OF THE DRAWINGS

The preferred embodiments of the present invention will hereinafter be described in conjunction with the accompanying drawings which are provided to illustrate and not to limit the invention, and, where like designations denote like elements throughout the drawings, and.

DETAILED DESCRIPTION OF THE PREFERRED EMBODIMENT

Figure 1:
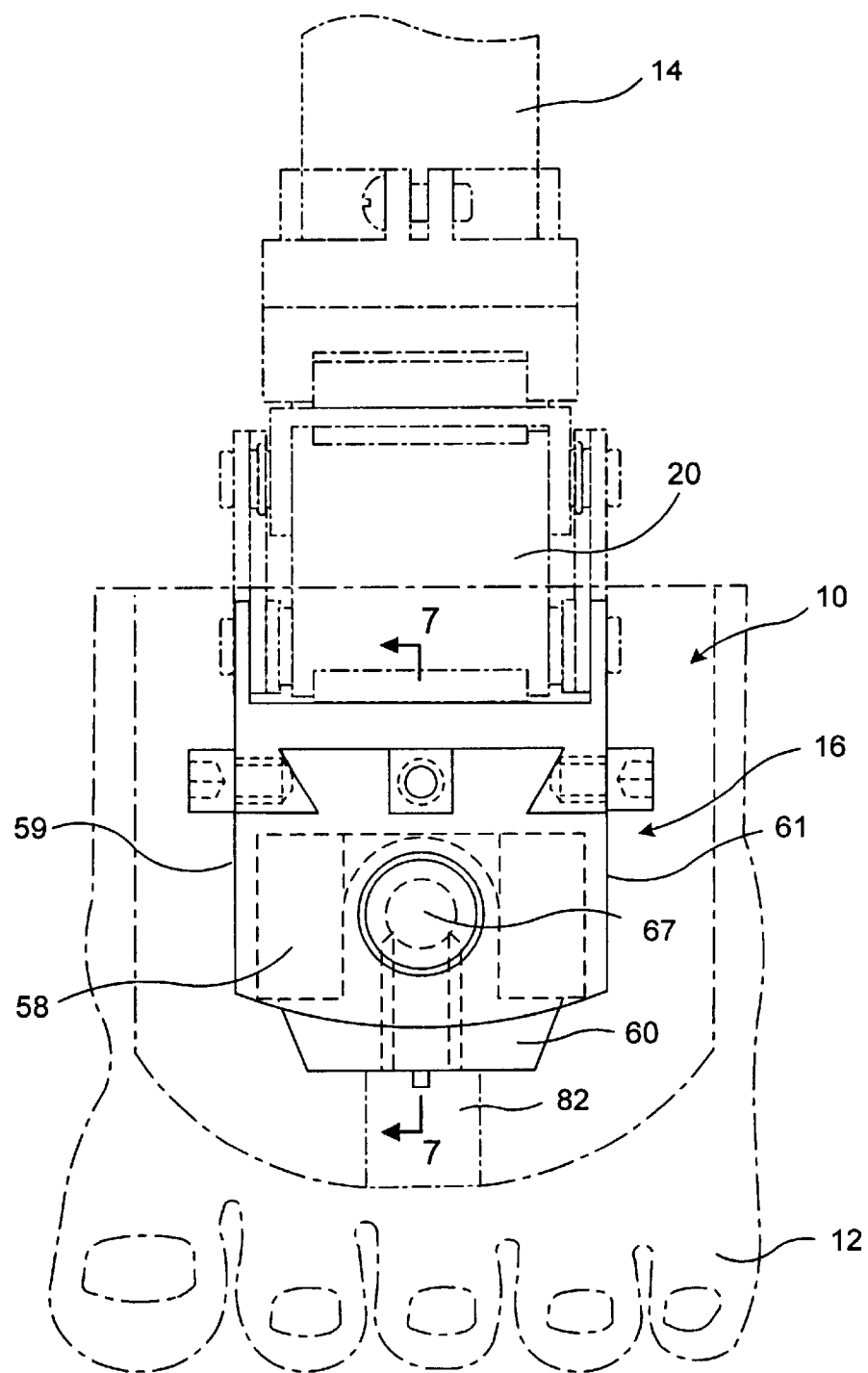
FIG. 1 is a front elevational view of a prosthetic ankle joint according to the invention.
Figure 2:
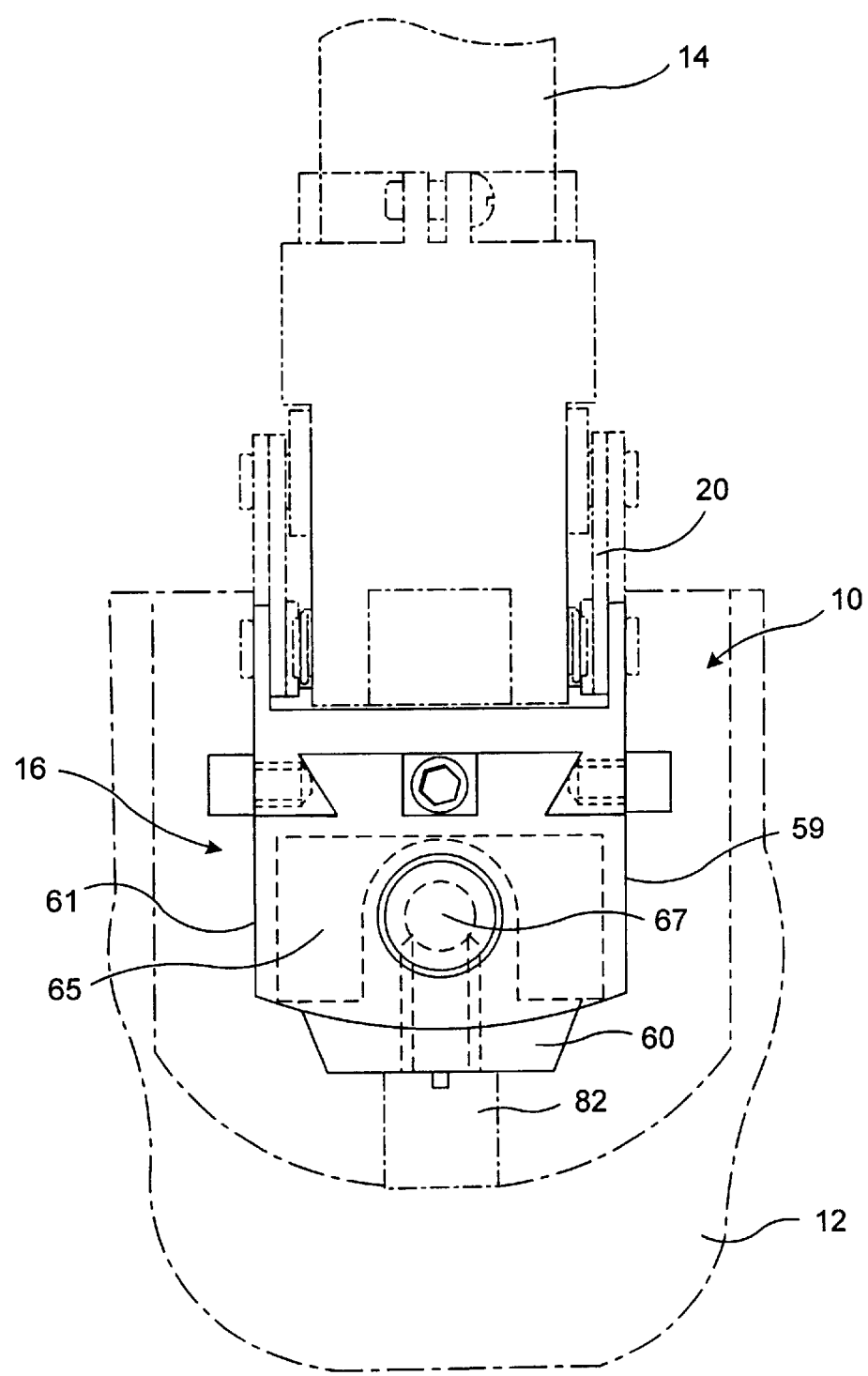
FIG. 2 is a rear elevational view thereof.
Figure 3:
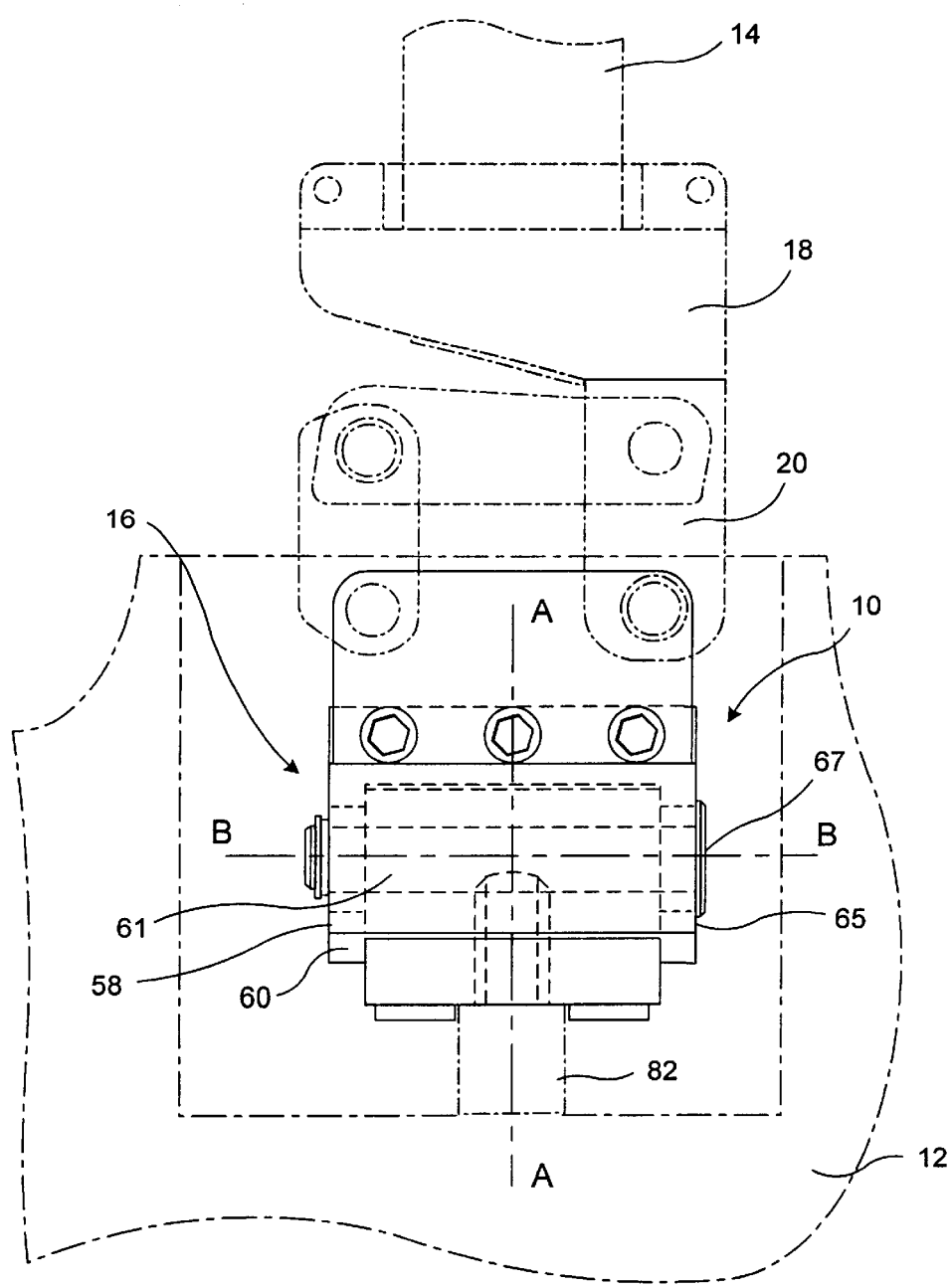
FIG. 3 is a side elevational view thereof.

Referring now to the drawings, and to FIGS. 1 to 3 in particular, a multi-axial prosthetic ankle joint 10 according to the invention is adapted for connection between a prosthetic foot 12 (shown in phantom line) and a prosthetic lower leg section or pylon 14 (shown in phantom line). The prosthetic ankle joint 10 includes a multi-axial base assembly 16, a four-bar linkage assembly 20 (shown in phantom line) pivotally connected to the base assembly 16 and the torque bracket 18 (shown in phantom line). The torque bracket and the linkage assembly (shown in phantom) have been fully described by U.S. Pat. No. 6,187,052 and do not form a part of the invention. The multi-axial base assembly 16 can be used with the linkage assembly 20 and bracket 18, as well as with other arrangements adapted for connection to the pylon and facilitating movement of the foot during human locomotion.

Figures 4A, 4B, 4C:
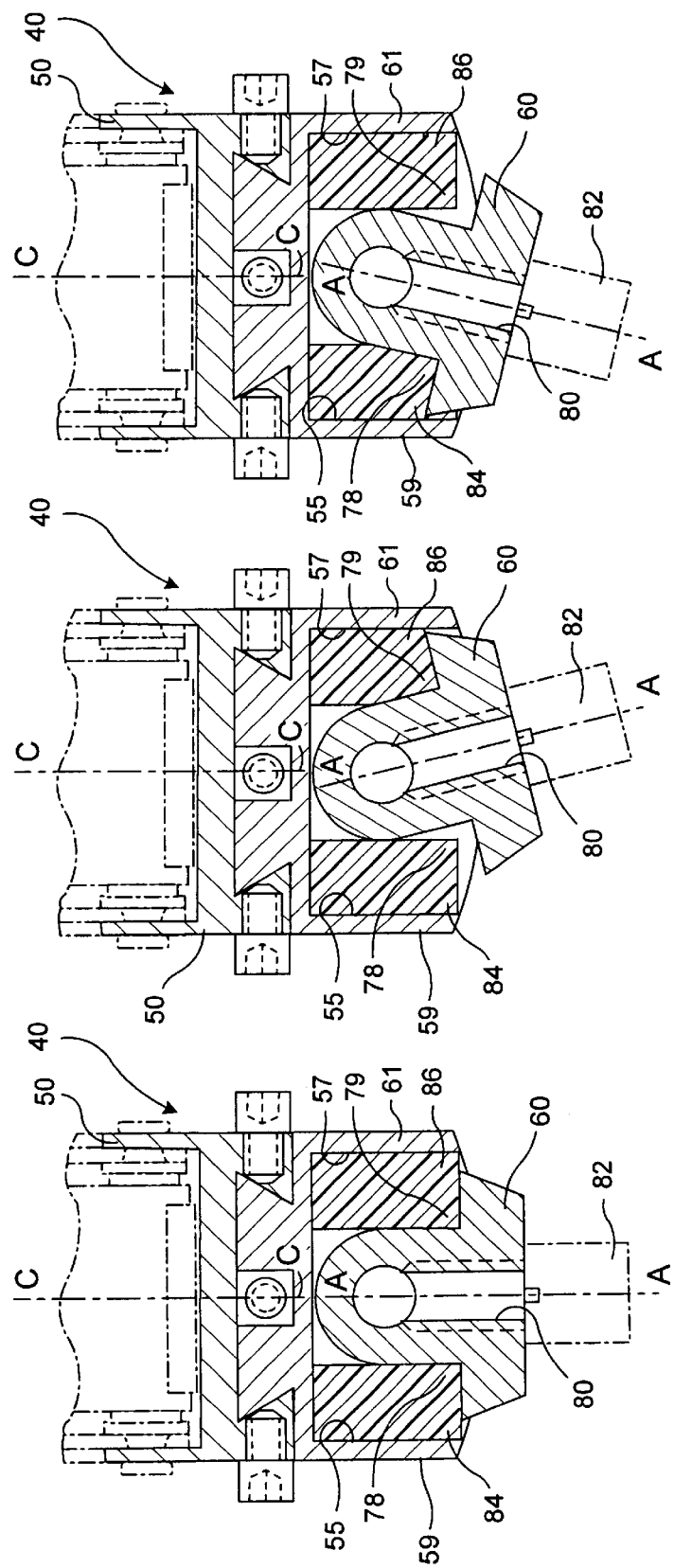
FIG. 4A is a section view showing a neutral position of the base member.
FIG. 4B is a section view showing another position of the base member.
FIG. 4C is a section view showing a further position of the base member.
Figure 5:
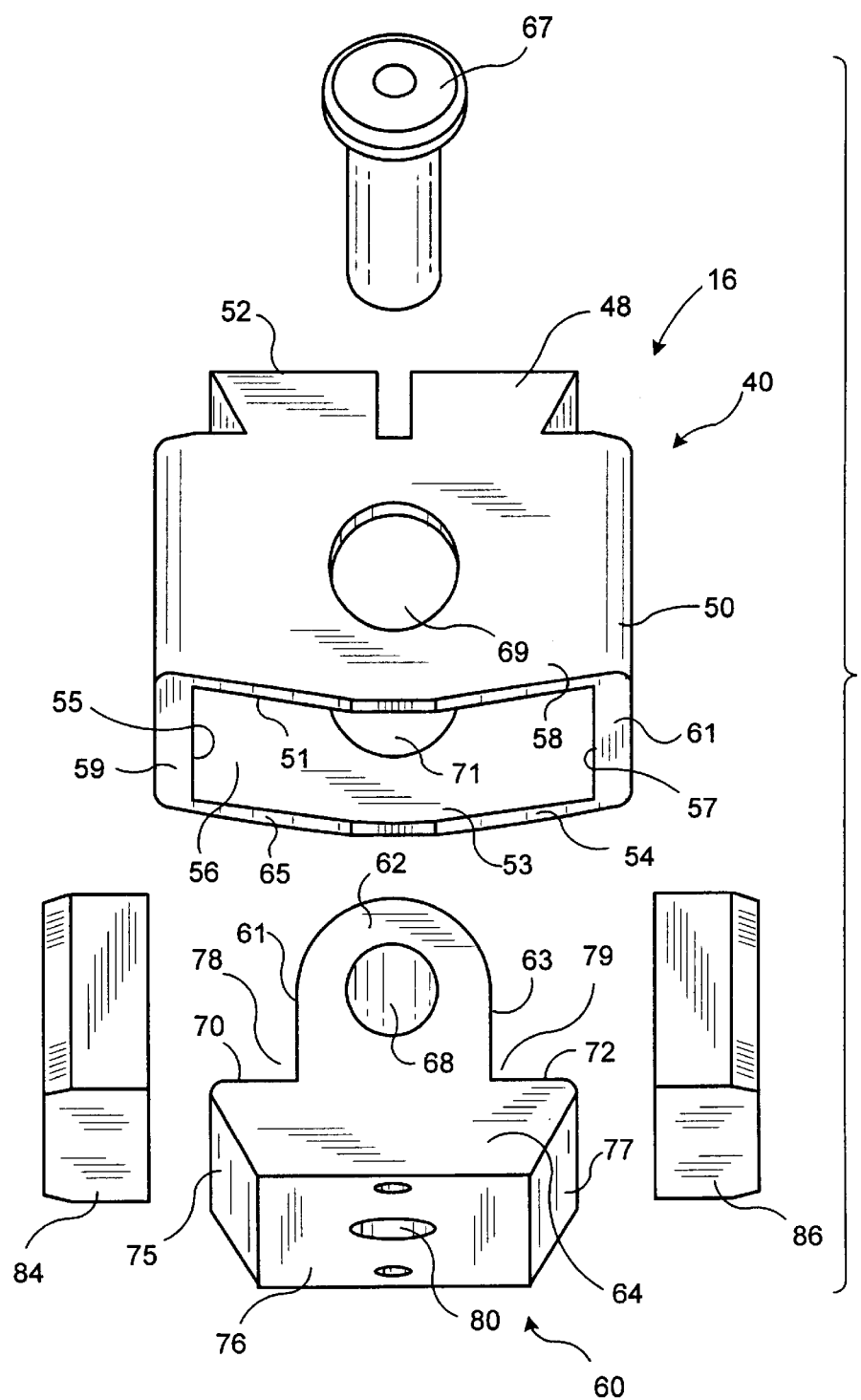
FIG. 5 is an exploded view of a base assembly.

Turning now to FIGS. 4 and 5, among essential elements of the multi-axial base assembly 16 are: a base 40, a base member 60 and biasing members 84 and 86. The base 40 extends between its proximal end 52 and a distal end 54 and is formed with an upper base portion 48 and a lower base portion 50. The base 40 is defined by an anterior wall 58 and posterior wall 65 which are interconnected by side walls 59 and 61. A substantially hollow receiving inner cavity 56 extends inwardly within the lower base portion 50 from an open distal end 54 and is formed by an anterior surface 51, posterior surface 53, first 55 and second 57 side surfaces which correspond to the anterior, posterior and side walls, respectively. The base member 60 is movably positioned within the receiving inner cavity 56.

The base member 60 is formed having an inverse T-shaped configuration and consists of an upright portion 62 which extends outwardly from a lower portion 64 having upper engaging sides 61, 63 which are spaced from each other and disposed symmetrically to an opening 68. As best illustrated in FIGS. 4 and 5, a top end of the upright portion is preferably rounded in shape. The substantially cylindrical opening 68 passes through an upper part of the upright portion 62 along a longitudinal axis B—B and is adapted to slidably receive a shaft 67. Shoulders or lower engaging sides 70 and 72 are provided on either side of the upright portion. Auxiliary sides 75 and 77 slope down from the respective shoulders towards the bottom part 76. The upper engaging side 61 and the lower engaging side 70 form a first engaging zone 78, whereas the upper engaging side 63 and the lower engaging side 72 define a second engaging zone 79. In the preferred embodiment of the invention the respective upper and lower engaging sides forming respective engaging zones are positioned to each other at a normal angle. However, other configurations of the engaging zones, where the respective engaging sides are positioned at acute or obtuse angle to each other, are also contemplated.

Anterior and posterior surfaces of the base member are substantially flat and situated in the planes which are transverse to the longitudinal axis B—B of the base member. A receiving hole 80 is provided within a central area of the bottom part 76 of the base member and adapted to receive a connecting rod or foot bolt 82 which provides connection between the base assembly 16 and the mounting area of the prosthetic foot 12. As best illustrated in FIGS. 1–3, the base member 60, the foot bolt 82 and the prosthetic foot 12 form a rigid unitary assembly.

The anterior 58 and posterior 65 walls are each formed with apertures 69 and 71, respectively. As best illustrated in FIGS. 1–5, in the assembled condition of the invention, the base member 60 is surrounded by the anterior 51, posterior 53, and side 55, 57 surfaces in such a manner that spaces or gaps are formed between the base member 60 and the receiving inner cavity 56. The base member 60 is movably supported within the inner cavity 56 by the shaft 67 which extends through the apertures 69 and 71 in the anterior and posterior walls and through the opening 68 in the upright portion. Such arrangement allows a limited arcuate or swivel motion of the base member 60 and the prosthetic foot 12 connected thereto relative to the lower base portion 50 and the inner cavity 56. In order to exercise control over such motion of the base member 60, a pair of biasing members 84 and 86 is freely positioned substantially symmetrically within the inner cavity 56. The biasing members 84, 86 are received by the first 78 and second 79 engaging zones of the base member 60.

The enclosed area within the inner cavity 56 is defined in one direction by the resilient biasing members 84 and 86 which encompass the spaces or gaps between the inner side surfaces 55, 57 and the base member 60. In the other direction, the enclosed area is defined by substantially flat anterior and posterior surfaces 51, 53 of the inner cavity which are spaced from substantially flat anterior and posterior surfaces of the base member 60. It will be discussed hereinbelow that containment of the spaces or gaps within the receiving inner cavity by the biasing members and their resilient spring function assure the controllable arcuate or swiveling motion of the base member from the fully extended inverted or everted position to the neutral position of equilibrium and vice-versa.

In the preferred embodiment the resilient biasing members 84 and 86 are freely positioned within the inner cavity 56 and are captured by the base member 60 and the inner surfaces of the cavity. It should be understood, however, that other methods of installation and positioning of the biasing members within the receiving inner cavity are within the scope of the invention.

It will be discussed hereinbelow that one of the major functions of the resilient biasing members 84 and 86 is to generate the required energy and to provide controllable resistance to the arcuate or swiveling motion of the base member 60 and its gradual return from the fully extended position to the neutral condition of equilibrium.

Figure 6:
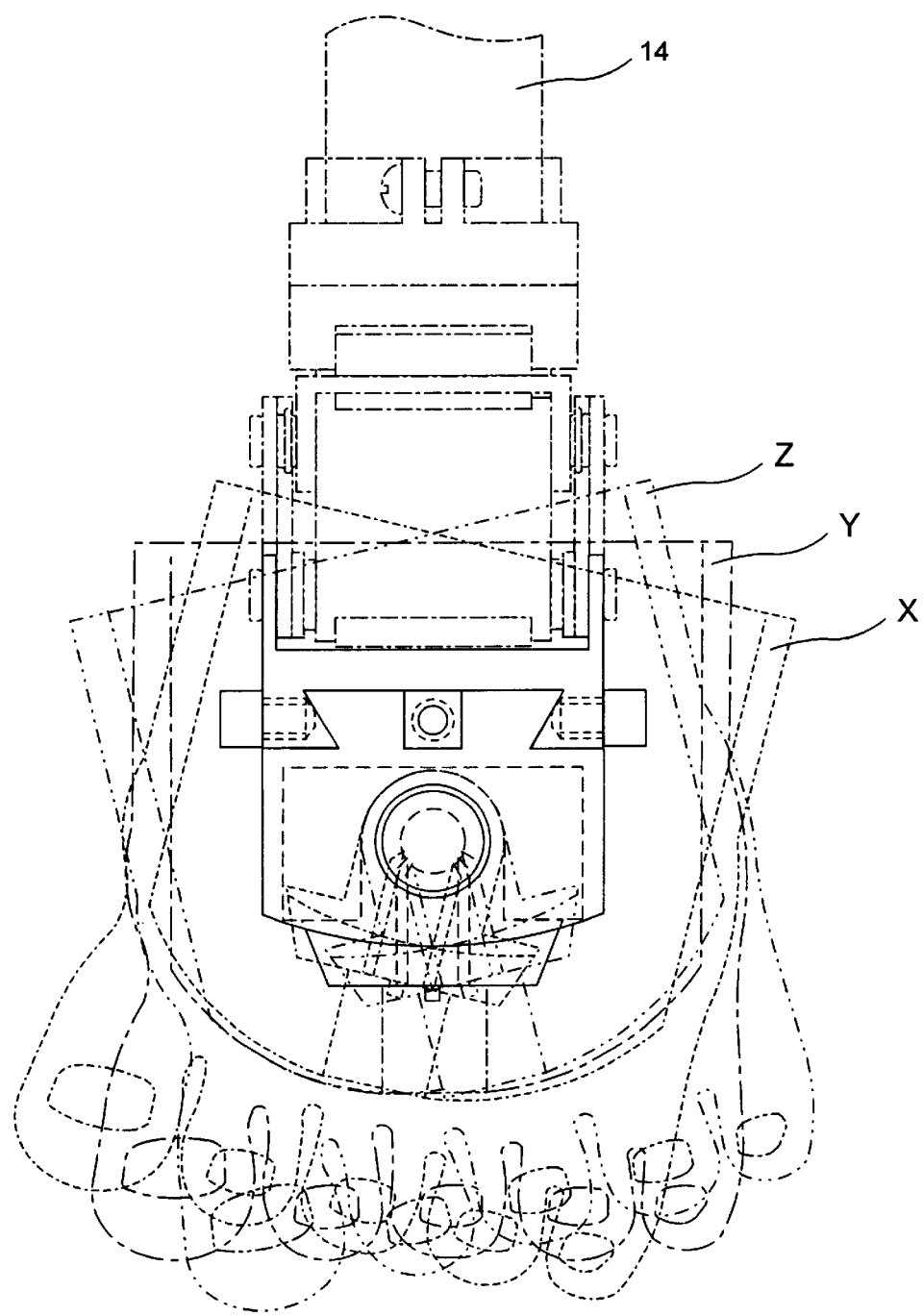
FIG. 6 is a front elevational view of the prosthetic ankle joint illustrating a range of motion between its various positions.
Figure 8:
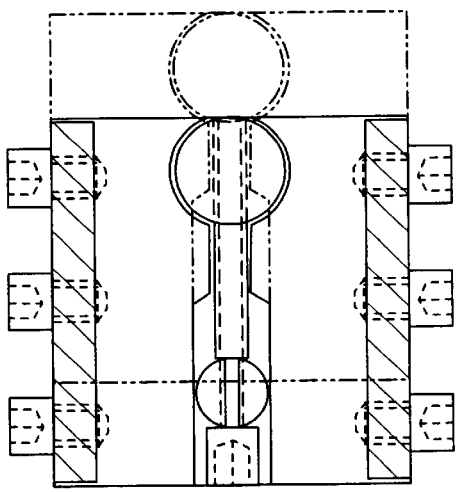
FIG. 8 is a section view according to section line 8—8 of FIG. 7.

Turning now to FIGS. 4 and 6, as the prosthetic foot 12 meets with different inclinations the ankle joint will adjust in the side to side direction, so as to allow the prosthetic foot to retain full and substantial contact with the inclined walkway surface. The multi-axial arrangement assures movement of the prosthetic foot between fully everted and fully inverted positions and return thereof to neutral position. The everted position of the prosthetic foot is represented in FIG. 6 by dash-double dot-line (see position Z) and is also illustrated in FIG. 4B. The neutral or medial position is represented in FIG. 6 by long dash-dot-line (see position Y) and is also shown in FIG. 4A. In a similar fashion the inverted position is represented in FIG. 4C and also shown by short dash-dot-line in FIG. 6 (see position X). In achieving the everted position, the base member 60 is directed toward the side wall 61 substantially diminishing the space between the base member and the inner side surface 57 of the inner cavity 56. This causes compression/deformation of the resilient biasing member 86 positioned therebetween. Upon the prosthetic foot disengaging the inclined surface the biasing member 86 tends to return to its balanced undeformed condition, causing the medial movement of the base member toward the neutral position. On the other hand, in achieving the inverted position, the base member 60 is being moved toward the side wall 59 compressing the biasing member 84. After the foot is relieved from its engagement with the respective inclined walking surface, the pressure exerted by the compressed biasing member 84 on the base member 60 results in its movement in the medial direction which is substantially terminated upon reaching the neutral position.

In use, as a prosthetic foot contacts a substantially flat walking surface (see FIG. 4a), the ankle unit is in the neutral position in which the base member is substantially vertical and the resilient biasing members 84, 86 are substantially undeformed. Therefore, the pressure exerted by the biasing members 84, 86 on both engaging zones 78, 79 of the base member 60 is balanced. In this condition the base member-foot bolt unitary assembly is centered and the transverse axis A—A of the base member substantially coincides with the vertical axis C—C of the base. This situation exists until extraneous forces are applied on one side or the other of the ankle unit resulted in arcuate or swiveling motion of the base member 60, which causes compression or deformation of the respective resilient biasing member. The extraneous forces are typically the result of the prosthetic foot engaging and the body weight being applied to uneven terrain. While the prosthetic foot engages an inclination of the walking surface, it is being placed in either inverted or everted position or any position therebetween. In this motion, while the respective biasing member being compressed/deformed, a predetermined amount of energy is generated and kinetically accumulated within the compressed biasing member. The ability to generate energy typically depends on the characteristics of material utilized for manufacturing of the biasing members and should be sufficient for self-centering function, so as to return the base member-foot assembly to the neutral position.

Reverting now to FIG. 4B which shows the multi-axial ankle joint in the everted position. As the prosthetic foot 12 engages an inclined surface, the base member 60 connected to the foot bolt 82 is arcuately moved toward the side surface 57 of the receiving inner cavity 56. In this manner, the space between the engaging zone 79 of the base member and the inner side surfaces 57 is decreased causing compression or deformation of the biasing member 86. In this position, the transverse axis A—A of the base member is positioned at an angle to the axis C—C of the base. In view of the resiliency and other qualities of the biasing member, sufficient energy is generated and accumulated within the compressed biasing member 86. After the foot disengages the inclined surface, the compressed biasing member 86 tends to return to its original shape releasing the accumulated energy and exerting pressure on the base member in general and the engaging zone 79 in particular. This pressure activates the self-centering function of the device and causes the arcuate or swiveling motion of the base member-prosthetic foot assembly in the medial direction. Such motion takes place until the base member 60 and the foot bolt 82 connected thereto reach the equilibrium or neutral position as illustrated in FIG. 4A. The medial movement to the neutral position is smooth and gradual as being controlled and compensated by the matching biasing member 84. Since the prosthetic ankle joint of the invention mimics movement of the human ankle in the preferred embodiment the range of the arcuate movement is between 0° and 15° to the horizontal plane.

In achieving the inverted position illustrated in FIG. 4C, the base member 60 is arcuately moved towards the side surface 55, so as to cause compression and/or deformation of the biasing member 84. The accumulated energy tends to return the biasing member 84 to its original shape by exerting pressure on the engaging zone 79 of the base member. Such pressure initiates the self-centering function and results in the arcuate motion of the base member in the medial direction until it reaches the balanced equilibrium position.

Figure 9:
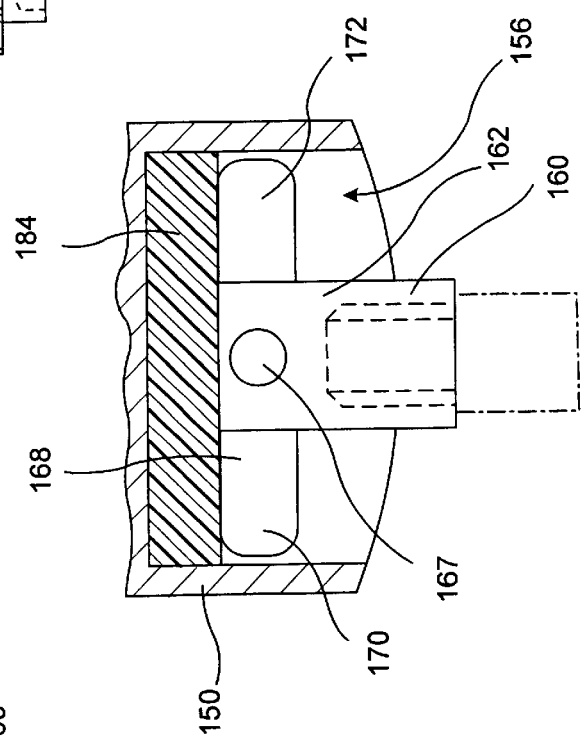
FIG. 9 is a section view of another embodiment of the invention.
Figure 7:
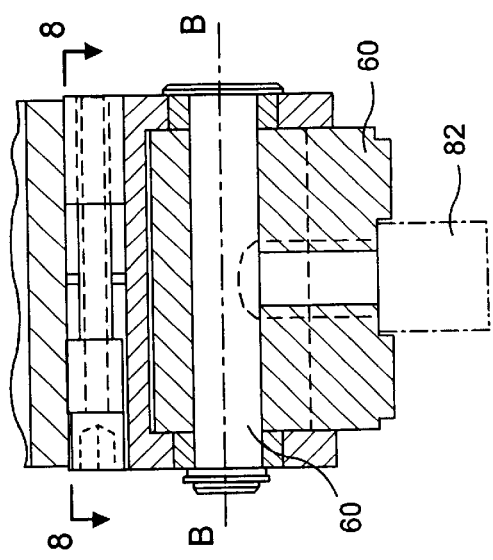
FIG. 7 is a partial section view according to section line 7—7 of FIG. 1.

Turning now to FIG. 9, wherein another embodiment of the multi-axial ankle joint of the invention is illustrated. The substantially hollow receiving inner cavity 156 extends inwardly within the lower base portion 150. The base member 160 having T-shaped configuration is movably positioned within the inner cavity 156. The base member consists of an upright portion 162 which extends outwardly from the engaging portion 168 having a first engaging portion 170 and a second engaging portion 172. A resilient biasing member 184 is freely positioned between the engaging portion 168 and the inner cavity. The shaft 167 movably supports the base member 160 within the lower base portion. The movement of the base member causes compression of the biasing member 184, so as to generate the energy necessary for returning the base member and the prosthetic foot connected thereto to the neutral position.

The provision of the above-discussed base member-prosthetic foot assembly capable of controlled movement from side to side results in the prosthetic ankle unit having a multi-axial motion that is capable of handling many combinations of walking surfaces including slopes in sideward directions that act upon the bottom of the foot, which usually make walking difficult for an amputee. Thus, the invention provides more efficient contact between the foot and the walking surface and also increases friction surfaces, so as to make the amputee more sure-footed.

It has been discussed hereinabove that the prosthetic multi-axial ankle joint of the invention is capable of generating enough energy and offering controlled resistance against movement of the prosthetic foot in the side to side direction. The amount of such required energy may vary, depending on the particular anatomical structure and needs of an individual user. For example, after the required surface contact between the prosthetic foot and an inclined walking surface has been obtained, in order to provide controllable, gradual return of the base member to the equilibrium state, a heavy person with a relatively long stride will require greater energy for the movement of the prosthetic foot than a light-weighted person with a relatively short stride. Depending on the height, weight, stride length and speed, shoe size, and other characteristics of a user, the resiliency and/or resistance to deformation of the biasing members may be adjusted by increasing or decreasing the durometer of the material utilized for their manufacturing.

The biasing members can be formed of many resilient materials having conventional configuration. However, in the preferred embodiment of the invention, the biasing members 84, 85, and 184 are made of an elastomer having a substantially rectangular cross section. Although the rectangular configuration is preferred, it is to be understood that the resilient biasing members may be formed with other crossections, such as semi-spherical, pyramidal, etc.

As to other possible variations, although a receiving inner cavity having a pair of resilient biasing members is preferred, an embodiment of the invention with at least one biasing member is also contemplated. This can occur when the biasing member is in the form of an integral insert made of a resilient material and provided for insertion into the inner cavity.

It is to be understood that the terms inner, outer, upper, lower, vertical, horizontal, upright, anterior, posterior, and their respective derivatives as used throughout the specification refer to relative, rather than absolute positions or orientations.

What is claimed is:

1. A prosthetic ankle joint for connection between a pylon and a prosthetic foot, the prosthetic ankle joint comprising:
   a bracket member adapted for connection to a pylon;
   a base consisting of an upper base portion and a lower base portion, said lower base portion is formed with a substantially hollow receiving inner cavity extending inwardly from an end thereof remote from the upper base portion;
   a base member movably positioned within the receiving inner cavity and connected to a prosthetic foot, said base member including a linear upright portion and a transverse portion, said transverse portion being transverse to the upright portion and connected to one end thereof, at least one resilient biasing member completely positioned within the receiving inner cavity adjacent said base member, said bracket member and said base being controllably movable in the anterior to posterior direction; and
   said base member and said prosthetic foot being controllably movable in the side to side direction independently of said base to enable said prosthetic foot to closely follow a walking surface.

2. The prosthetic ankle joint according to claim 1, wherein said upright and transverse portions define the base member having an inverse T-shaped configuration which is arcuately movable within said receiving inner cavity.

3. The prosthetic ankle joint of claim 2, wherein the base member further comprises the upright portion defined by at least first and second upper engaging portions spaced from each other, the upright portion extends outwardly from the transverse portion in such a manner that first and second lower engaging portions are formed on either side of the upright portion, so that the first upper engaging portion and the first lower engaging portion define a first engaging zone and the second upper engaging portion and the second lower engaging portion forming a second engaging zone.

4. The prosthetic ankle joint according to claim 3, wherein said first tapper engaging portion is substantially normal to said first tower engaging portion and said second upper engaging portion is substantially normal to said second lower engaging portion.

5. The prosthetic ankle joint according to claim 3, wherein the lower base portion is formed with anterior and posterior walls interconnected by side walls, and coaxial apertures are formed within the anterior and posterior walls.

6. The prosthetic ankle joint according to claim 5, wherein the upright portion of the base member contains an opening passing therethrough, the base member is movably supported within the lower base portion by a shaft passing through the apertures in the anterior and posterior walls and the opening in the upright portion.

7. The prosthetic ankle joint according to claim 1, wherein said at least one resilient biasing member comprises a pair of resilient biasing members which are positioned within the inner cavity, so as to face the respective first and second engaging zones of the base member.

8. The prosthetic ankle joint according to claim 7, wherein the arcuate motion of the base member in medial and lateral directions is limited by the resilient biasing members.

9. The prosthetic ankle joint according to claim 8, wherein the arcuate motion of the base member mimics the motion of the human ankle, wherein the range of such motion is between 0° and 15° to the horizontal plane.

10. The prosthetic ankle joint according to claim 7, wherein an enclosed area is defined within the inner receiving cavity in one direction by the pair of biasing members facing the engaging zones of the based member; and in the other direction said enclosed area is defined by the inner surfaces of the anterior and posterior walls positioned in the vicinity of substantially flat anterior and posterior surfaces of the base member.

11. The prosthetic ankle joint according to claim 10, wherein during the arcuate motion of the base member a distance between the respective engaging zone of the base member and the inner cavity is decreased causing deformation of the respective biasing member interposed therebetween.

12. The prosthetic ankle joint according to claim 11, wherein the deformed biasing members forces the base member back to the neutral position in which a vertical axis of the base member substantially coincides with the transverse axis of the lower base portion.

13. The prosthetic ankle joint according to claim 12, wherein positioning of the base member within the receiving inner cavity between the biasing members provides a self-centered arrangement which is adapted to return the base member to the neutral position.

14. The prosthetic ankle joint according to claim 7, wherein said resilient biasing members are freely positioned within the receiving inner cavity and captured between the inner surfaces of the respective side walls and the respective engaging zones of the base member.

15. The prosthetic ankle joint according to claim 7, wherein the resilient biasing members are made of a material selected from the group consisting of urethane and rubber.

16. The prosthetic ankle joint according to claim 1, wherein said upright and transverse portions define the base member having a T-shaped configuration which is arcuately movable within said receiving inner cavity.

17. A prosthetic ankle joint for connection between a pylon and a prosthetic foot, the prosthetic ankle joint comprising:

a bracket member adapted for connection to a pylon;

a base consisting of an upper base portion and a lower base portion, said lower base portion is formed with a substantially hollow receiving inner cavity extending inwardly from an end thereof remote from the upper base portion, a base member movably positioned within the receiving inner cavity, the base member is connected to a prosthetic foot;

said base member having an inverse T-shaped configuration and comprises an upright portion extending outwardly from the lower portion so as to form first and second engaging zones on either side of the base member; a pair of resilient biasing members is provided within the receiving inner cavity to face the respective first and second engaging zones and to limit and control the arcuate motion of the base member.

18. The prosthetic ankle joint according to claim 17, the base member further comprises first and second upper engaging portions spaced from each other and first and second lower engaging portions extending outwardly from the first and second upper engaging portions, the first upper engaging portion and the first lower engaging portion forming the first engaging zone and the second upper engaging portion and the second lower engaging portion forming the second engaging zone, the upright portion of the base member contains an opening passing through its upper region, the base member is movably supported within the lower base portion by a shaft passing through the apertures in the anterior and posterior walls and the opening in the upright portion.

19. The prosthetic ankle joint according to claim 18, wherein during the arcuate motion of the base member a distance between the engaging zone of the base member and the inner cavity is decreased causing deformation of the respective biasing member positioned therebetween.

20. The prosthetic ankle joint according to claim 17, wherein the range of arcuate motion of the base member and the prosthetic foot connected thereto is between 0° and 15° to a horizontal plane.

* * * * *